United States Patent
Guenther

(10) Patent No.: US 8,260,396 B2
(45) Date of Patent: Sep. 4, 2012

(54) EXTREME SPEED-UP OF ACQUISITION OF PERFUSION TIME SERIES BY CYCLED ARTERIAL SPIN LABELING MRI

(75) Inventor: Matthias Guenther, Bruchsal (DE)

(73) Assignee: Advanced MRI Technology, LLC, Sebastopol, CA (US)

( * ) Notice: Subject to any disclaimer, the term of this patent is extended or adjusted under 35 U.S.C. 154(b) by 634 days.

(21) Appl. No.: 12/086,549

(22) PCT Filed: Sep. 19, 2006

(86) PCT No.: PCT/US2006/036681
§ 371 (c)(1),
(2), (4) Date: Jan. 22, 2009

(87) PCT Pub. No.: WO2007/035824
PCT Pub. Date: Mar. 29, 2007

(65) Prior Publication Data
US 2009/0149733 A1    Jun. 11, 2009

(51) Int. Cl.
A61B 5/00    (2006.01)
(52) U.S. Cl. .................. 600/410; 324/307; 324/309
(58) Field of Classification Search .......... 600/407, 600/410, 411, 419; 324/306–309
See application file for complete search history.

(56) References Cited

U.S. PATENT DOCUMENTS

| 5,846,197 | A | 12/1998 | Edelman |
| 6,271,665 | B1 | 8/2001 | Berr et al. |
| 6,564,080 | B1 | 5/2003 | Kimura |
| 7,587,233 | B2 * | 9/2009 | Wong et al. ................ 600/419 |
| 2003/0216636 | A1 * | 11/2003 | Paley et al. ................ 600/410 |
| 2004/0027124 | A1 * | 2/2004 | Abe et al. ................... 324/306 |
| 2004/0204643 | A1 | 10/2004 | Jesmanowicz |
| 2005/0277828 | A1 | 12/2005 | Alsop |
| 2006/0210543 | A1 | 9/2006 | Leor et al. |
| 2008/0269595 | A1 * | 10/2008 | Wong ......................... 600/411 |

OTHER PUBLICATIONS

Apr. 12, 2011 European search report in connection with counterpart European patent application No. 06 82 5037.
Chao, Hui, et al. (1997), "Multibolus Stimulated Echo Imaging of Coronary Artery Flow," Journal of Magnetic Resonance Imaging, vol. 7, pp. 603-605.
Kao, Yi-Hsuan, et al. (1998), "Simultaneous Multislice Acquisition with Arterial-flow Tagging (SMART) using Echo Planar Imaging (EPI)," Magnetic Resonance in Medicine, vol. 39, pp. 662-665.
Wong, E.C., et al. (2005) "Vascular Source Imaging," Proceedings of the International Society for Magnetic Resonance in Medicine, 13, p. 1131.
Guenther, M., (2007), "Highly efficient accelerated acquisition of perfusion inflow series by Cycled Arterial Spin Labeling," Proceedings of the International Society for Magnetic Resonance in Medicine, 15, p. 380.

* cited by examiner

Primary Examiner — Brian Casler
Assistant Examiner — Amanda Lauritzen
(74) Attorney, Agent, or Firm — Cooper & Dunham LLP

(57) ABSTRACT

Quantitative assessment of haemodynamics by cycled arterial spin labeling (CACL) that distinguishes between blood magnetization tagged by a specific labeling pulse, using a time series acquisition in which all measured data sets are used for reconstruction of each single time step, thereby reducing measurement time while maintaining signal-to-noise ration compared to conventional ASL.

15 Claims, 4 Drawing Sheets

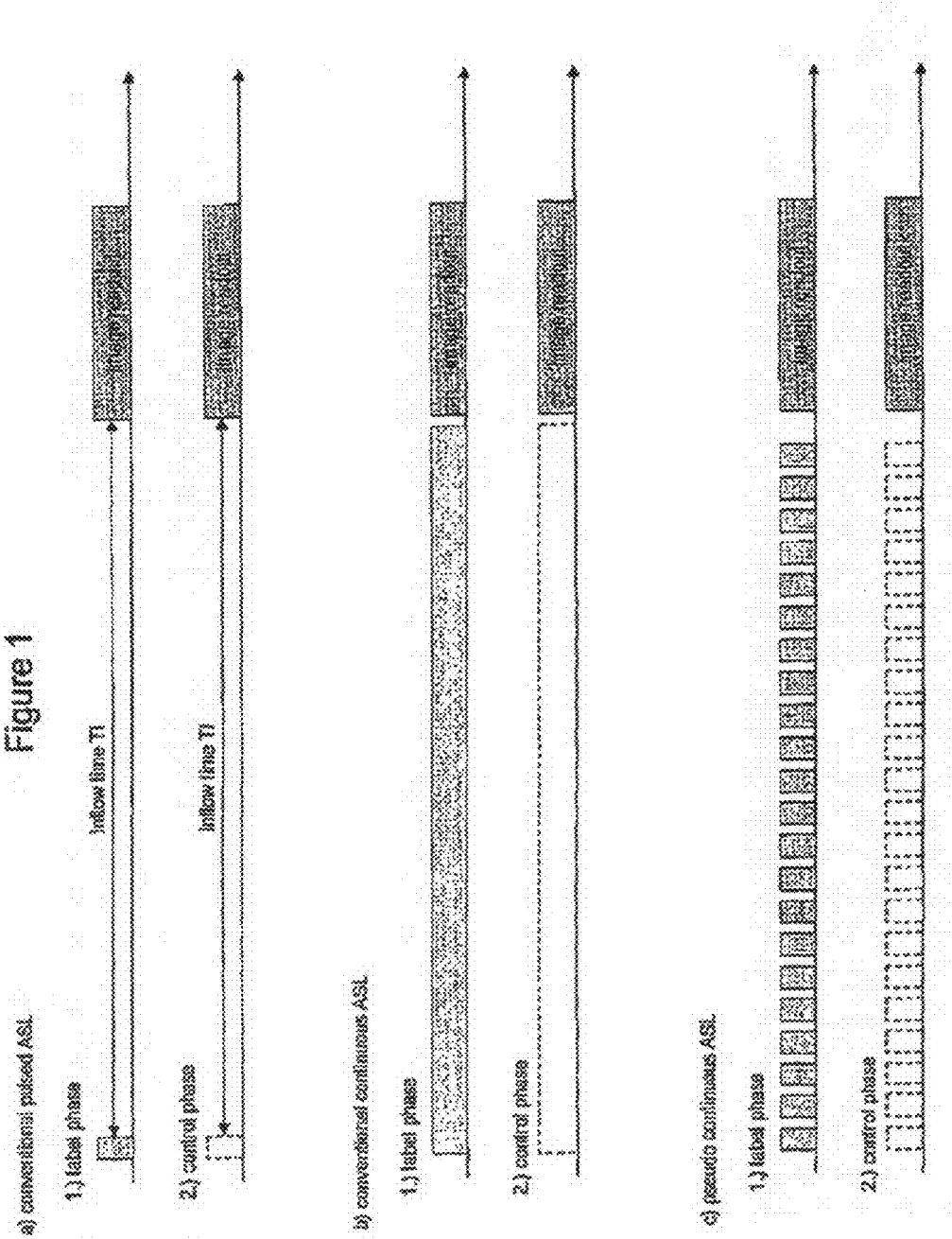

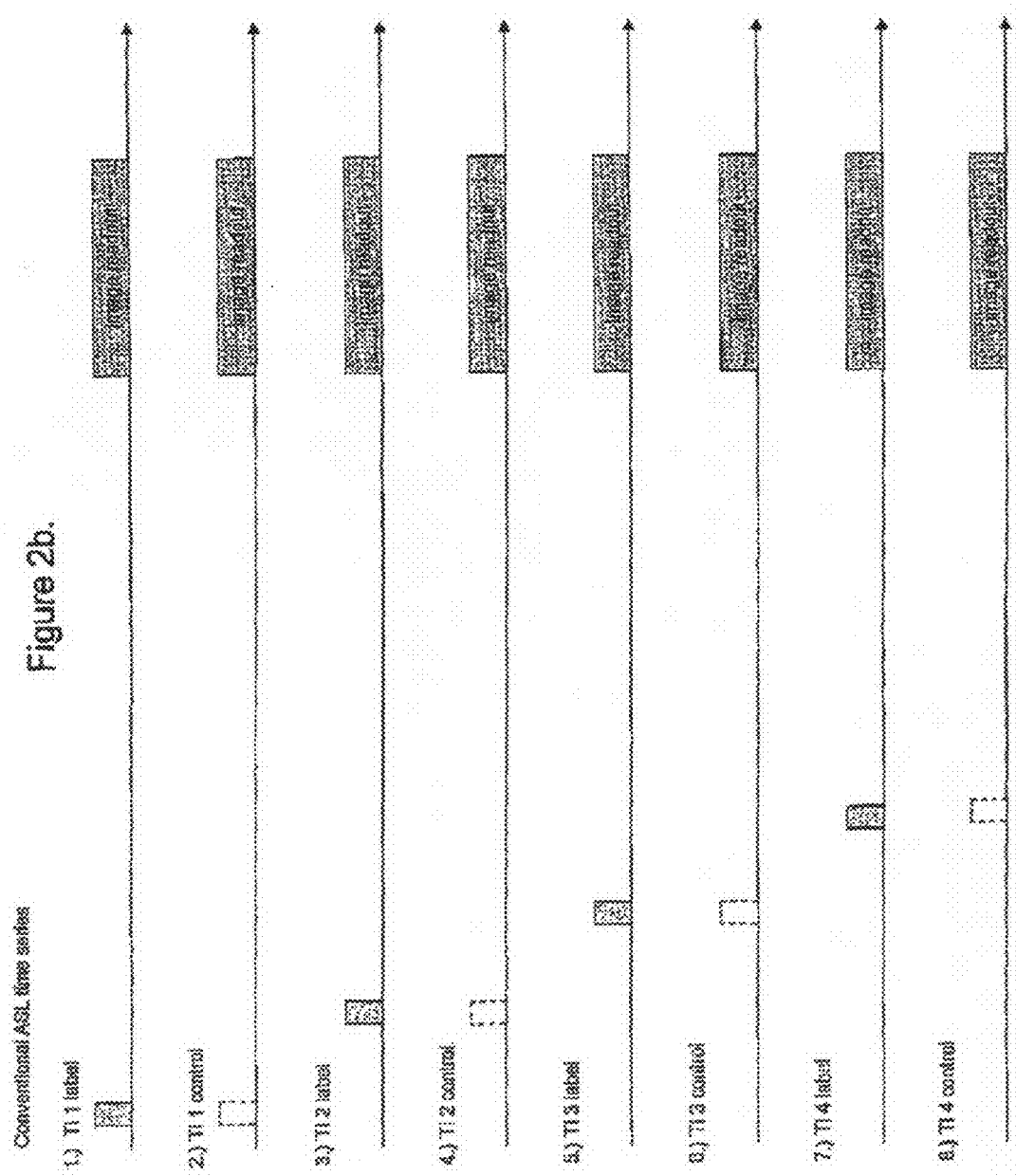

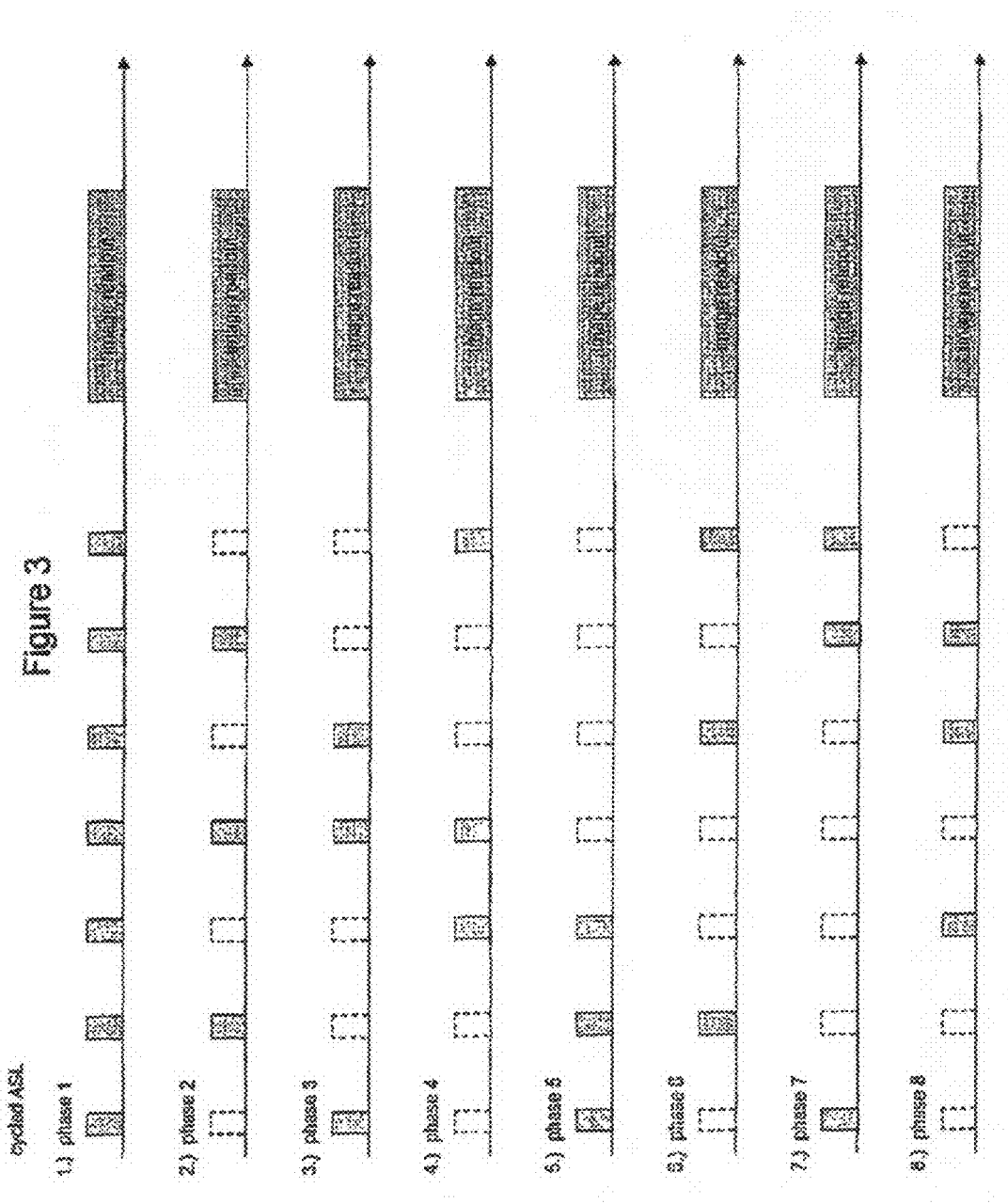

EXTREME SPEED-UP OF ACQUISITION OF PERFUSION TIME SERIES BY CYCLED ARTERIAL SPIN LABELING MRI

BACKGROUND

Quantitative assessment of cerebral haemodynamics is essential for reliable estimation of organ state and function. Magnetic resonance imaging (MRI) has shown the ability to provide this information in a noninvasive manner. Especially, arterial spin labeling (ASL) (1-4) is a technique that avoids use of extrageneous contrast agent by using magnetic tagging of inflowing blood spins. (The numerals in parenthesis throughout this patent specification refer to the 14 references cited at the end of the disclosure, all of which are hereby incorporated by reference.) In principle, ASL is capable of providing quantitative estimation of haemodynamics parameters such as cerebral blood flow (CBF) with less theoretical assumptions than other known techniques. ASL typically comprises two phases, one labeling and one control phase. In the labeling phase blood water spins flowing into a slab of interest are inverted upstream by radio frequency (RF) pulses and after an inflow time TI an image of the slab is acquired. In the control phase, the inflowing blood water spins remain uninverted before the image is acquired after TI. The data sets of both phases are subtracted to cancel out signal of stationary tissue and only yield signal of the inflown blood.

There are several techniques which achieve this tagging but usually they can be divided up in two groups: pulsed and continuous ASL. The main difference of these groups is the length of the labeling process that occurs either once for a short period of time (typically less than 50 ms, see FIG. 1a) or over multiple seconds (continuous, see FIG. 1b; and pseudo continuous, see FIG. 1c). It was shown that both groups are useful to estimate local perfusion. However, absolute quantification of CBF is affected by the fact that the time the blood needs to flow to different regions of the imaging slab (so called bolus arrival time, BAT, or arterial transit time, ATT) varies. This is one reason that has kept ASL from becoming a clinical routine tool. In conventional pulsed ASL (PASL) as illustrated in FIG. 1a, the blood is labeled at a specific point in time and in a large spatial region, producing a certain bolus of labeled blood. This bolus will have a certain time of arrival in a downstream imaging voxel of interest. The longer the inflow time TI the larger the amount of labeled blood in this voxel. At a certain point in time the end of the bolus will arrive in the voxel so that the amount of labeled blood within the voxel will remain constant (assuming no relaxation and venous outflow). In continuous ASL (CASL) as illustrated in FIG. 1b, blood is labeled over a longer period of time in a small spatial region. Thus, for a given time (usually several seconds) labeled blood is flowing into the imaging slab. At the time the image is acquired there exists a steady state of the labeled blood in the imaging slab and a larger extent of the vascular tree will be filled with labeled blood. Since the inflow of labeled blood occurs over several seconds no arrival time can be derived from the acquired data. Pseudo-continuous ASL, as illustrated in FIG. 1c, represents a variant of CASL in which the continuous application of the labeling (and control) pulse is broken of into several short time pulses. This will have the same effect as one long pulse as long as all the inflowing blood experience the labeling effect. The pseudo-CASL can be used to reduce SAR problems at higher field strengths.

Several approaches exist to address problems in the above-described approach. They can be categorized in either diminishing the effect of different BAT or somehow measuring BAT and correcting for it. The first goal can be achieved by delaying the image acquisition to longer inflow times (5) or by limiting the length of the bolus by additional saturation pulses upstream the imaging slice a certain time before image acquisition (QUIPSS II (6) and Q2TIPS (7)). However, all these techniques have in common that the signal-to-noise ratio (SNR) of the resulting perfusion images, which is already intrinsically low, is decreased even further. Furthermore, there exists no simple known method to ensure that the requirements for precise parameter estimation are fulfilled, which can be a major obstacle especially in pathologic cases.

Therefore, the most accurate way to measure CBF without dependency on BAT is to acquire a time series with multiple different TI. This allows direct estimation of BAT and correction for it using appropriate theoretical modeling. However, acquisition of time series is very time consuming due to the intrinsic low SNR of ASL. Measurement times of 30 minutes or more are common (e.g. (8)). Recently, a more efficient readout module in combination with ASL was presented (9), which allows reduction of the measurement time while maintaining the same SNR level but the problem still persists.

Another approach for more rapid acquisition of ASL time series is the measurement of more than one data set at different times TI after the labeling RF pulses. This technique is called inflow turbo sampling flow alternating inversion recovery (ITS-FAIR) (10) and is based on a Look-Locker readout in combination with an EPI-readout (REF). The basic idea is to utilize the labeled magnetization for multiple image readouts by using low flip angle RF pulses as excitation pulses. Each of those data sets will have a different TI and principally allows the acquisition of a time series within a single labeling cycle. There is no significant gain in SNR per measurement time compared to conventional ASL since the amount of labeled magnetization remains the same and is just split up. However, for quick evaluation of local BAT this method has proven useful (11). However, this technique is combined with gradient echo based readout modules, for otherwise the refocusing pulses will destroy most of the labeled magnetization.

To capture the dynamic of the inflow of the labeled blood into an imaging voxel of interest, the inflow time TI (time between application of the labeling (or control) pulses and actual image acquisition) is varied between successive experiments, as illustrated in FIG. 2a. To acquire a complete time series of, for example, 20 different TIs, at least 20 complete experiments have to be performed. This is very time-consuming, since several repetitions a necessary to provide sufficient signal. FIG. 2b illustrates a more time-efficient way to acquire time series is the ITS-FAIR technique (10), which uses low flipangle excitation pulses to sample the inflow curve of the labeled blood at several different TI after each labeling/control pulse. In theory, only one experiment is needed to acquire a whole time series of 20 different time points. In practice, however, due to low signal, multiple repetitions are needed and additional saturation effects lead to poor signal in the micro-vasculature.

In continuous ASL (CASL) the amount of labeled blood magnetization present in the imaging slab is greater than in pulsed ASL (PASL) since a labeling RF pulse is applied for a longer period of time. Therefore, in CASL the measured signal is based on a steady-state condition while it originates from a single bolus in PASL. By using more than one labeling RF pulse per cycle in PASL it is possible to increase the amount of tagged blood magnetization. For coronary bolus tagging MR angiography this was presented recently (12) to improve the filling of downstream vessels. The acquired data sets then include signal of labeled blood magnetization which was tagged at different times. However, it is difficult to tell which part of the signal originates from which labeling pulse.

SUMMARY

In this patent specification, a method is presented that enables distinction between blood magnetization tagged by a specific labeling pulse. The method allows the acquisition of time series in a very efficient way since all measured data sets are used for reconstruction of each single time step. Therefore, a 32-fold or more reduction of measurement time is given by maintaining the same SNR level of a conventional experiment.

In a non-limiting example of the new method, a different combination of a control and a label pulse is used in each time step and MRI readout is done for each step, while in the conventional ASL variant discussed above a readout is done for either control or labeling pulses but not for a combination of both.

BRIEF DESCRIPTION OF DRAWINGS

FIG. 1a illustrating conventional arterial spin labeling (ASL), FIG. 1b illustrating conventional continuous arterial spin labeling (CASL), and FIG. 1c illustrating pseudo continuous arterial spin labeling (PASL).

FIG. 2b illustrates a more efficient way to acquire time series using low flappable excitation pulses to sample the inflow curve of the labeled blood at several different times.

FIG. 3 illustrates a non-limiting example of cycled arterial spin labeling (CASC) according to the disclosure in this patent specification, in which there is a single readout after several labeling pulses each producing a respective bolus of labeled blood, and time series and labeling pulses for each bolus are varied in a cycling sequence to allow unique identification of the bolus.

DETAILED DESCRIPTION OF PREFERRED EMBODIMENTS

Figure 2A:
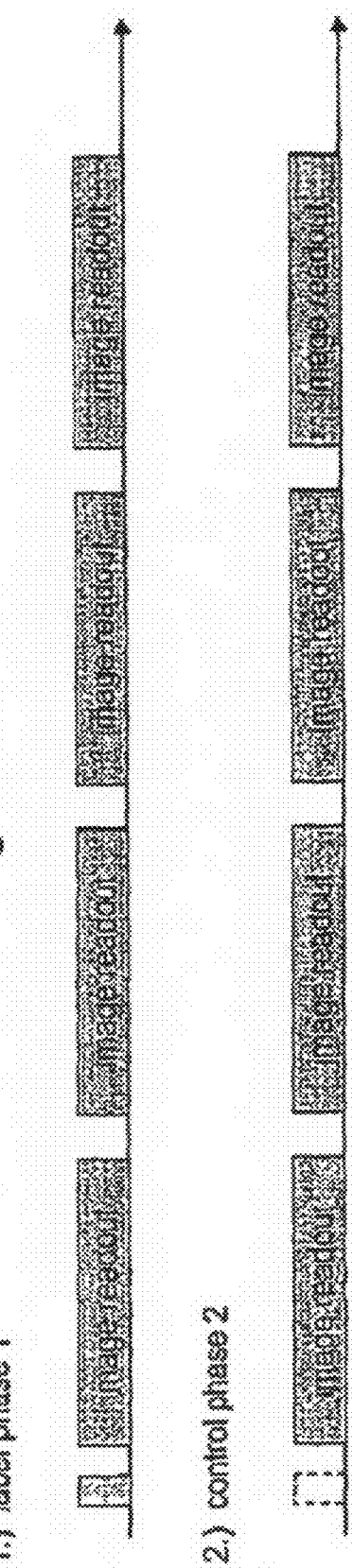
FIG. 2a illustrates acquisition of time series in which the time between application of the labeling and control pulses and actual image acquisition is varied between successive experiments.

The goal is to acquire data sets which comprise signal of multiple labeled blood boluses and to extract the signal of each single bolus. Since these boluses were labeled at different times before image readout, an ASL time series can be extracted. The differentiation requires an encoding of each bolus. As stated above, two phases, a control and label phase, are used to form a bolus of labeled blood. Using different combinations of control and label phase for each time step makes it possible to separate the signal of different boluses. In the following, the complete set of the combinations used to separate all boluses will be called a tagging cycle while a single combination will be dubbed a cycle step. The length of the tagging cycle is N.

The encoding problem can then be described by a matrix equation:

$$I = E \cdot M, \quad (Eq.1)$$

where $M = (M(TI_1), M(TI_2), \ldots, M(TI_N))^T$ is the fresh longitudinal magnetization of blood spins at the tagging side at times $TI_1$ to $TI_N$. The encoding matrix E describes whether a control or a labeling pulse is applied at time $TI_I$ for a given cycle step. The elements of E are either +1 or −1 for control or labeling phase, with rows representing each tagging cycle step. Vector I represents the data sets that are acquired in each cycle step. Therefore, the results of the encoding are N image data sets which comprise information from each bolus, either labeled or not. The signal of each bolus can then be reconstructed by inverting Eq.1 if certain restrictions to the encoding matrix E apply:

$$M = E^{-1} \cdot I, \quad (Eq.2)$$

The row vectors of E are independent, i.e. E has to be unitary. Since the elements of E are real, matrix E is orthogonal (i.e. $E' \cdot E = 1$, where E' is the transpose of E and 1 is the unitary matrix). An additional restriction applies: the sum of each row vector of E has to be zero. This restriction is caused by the basic idea of ASL to suppress the signal of the stationary tissue by subtracting a control and label phase. To maintain this ASL condition the same number of control and label images has to be subtracted to reliably cancel out the signal of the stationary tissue spins.

Several matrices exist, which fulfill these restrictions. However, it is not a trivial task to construct them for an arbitrary N. A well-known class of matrices, which substantially fulfills the requirements, is called Hadamard matrices. Hadamard matrices are defined recursively. They exist only for size $2^n$, for $n \in \mathbb{N}$.

The definition is:

$$H_1 = 1, \quad H_{N+1} = \begin{matrix} H_N & H_N \\ H_N & -H_N \end{matrix} \quad (Eq. A1)$$

Example for N=4:

$$H_4 = \begin{matrix} +1 & +1 & +1 & +1 \\ +1 & -1 & +1 & -1 \\ +1 & +1 & -1 & -1 \\ +1 & -1 & -1 & +1 \end{matrix}$$

Except for the first, all row vectors have the same number of +1 and −1 elements, i.e. the sum of each row vector is 0, except for the first where the sum is N.

With Hadamard matrices of size N, exactly N−1 different TIs can be encoded. FIG. 3 shows the whole label cycling experiment for N=8. Here, the first row vector of the Hadamard matrix is ignored since it does not fulfill the proper condition of zero summing. Therefore, seven different inflow times can be acquired by an eight step cycle. However, since all eight data sets in different combinations are used to reconstruct each image for a certain inflow time (only consisting of the signal of a single bolus), the SNR of each of the seven images will be as high as for a data set acquired by conventional ASL. Thus, using cycled ASL as proposed in this patent specification, a reduction in measurement time of factor N−1 (7 in this example) can be achieved by maintaining the same SNR compared to standard ASL time series experiments.

As illustrated in the example of FIG. 3, Instead of using several readouts after one labeling/control pulse as in the ITS-FAIR technique, Cycled ASL (CASL) in accordance with this patent specification uses in this non-limiting example several labeling pulses before a single readout. In conventional PASL one bolus of labeled blood is produced which is produced at a certain point in time and is acquired at a certain time. In Cycled ASL several boli of labeled blood are produced at different points in time and those boli are acquired a one point in time. Thus, the resulting data will be a mixture of all different boli which already arrived at the imaging site at the time of the acquisition. To be able to distinguish the different boli and reconstruct the time series, control and labeling pulse for each bolus are varied in a certain cycling scheme which allows unique identification of the bolus. The correct order of control and labeling pulses for each phase and bolus can be calculated using a Hadamard matrix. Since all acquired data sets are used for reconstruction of each bolus the SNR of each reconstructed data set at the inflow time TI is maximized.

In a practical application of the principles discussed above, five subjects (30-44y) were examined on a clinical 1.5 T MR-Scanner (Magnetom Sonata, Siemens, Erlangen, Germany) with maximum gradients of 40 mT/m and a minimum rise time to full gradient strength of 200 µs.

The encoding scheme based on Hadamard matrices was used to tag the magnetization of multiple blood boluses within a label cycling step. This mixture of signal tagged at different times before readout were acquired with a fast single shot 3D-GRASE readout technique (9) used with the following parameters: echo time TE=36 ms, repetition time TR=3750 ms, off-resonance fat saturation pulse, 28 interpolated partitions (16 acquired, ⅝ Fourier). A substantially isotropic resolution of 4.7 mm×4.7 mm×4.5 mm was achieved. Two averages of a 16-step label cycling were used (total acquisition time: 2 min), inflow times ranging from TI=200 ms to 3200 ms, increment 200 ms.

To avoid residual signal in the resulting images due to different magnetization transfer effects during control and labeling pulses, a modified TILT (13) scheme was used as described in (14). Instead of using +90°/−90° RF pulse combinations for control and +90°/+90° RF pulses for labeling as in TILT, the modified scheme uses one or two 180° adiabatic (hyperbolic secant) inversion pulses. Thickness of labeling band was 100 mm. A four RF pulse train for saturation was applied in the imaging slab before starting the tagging pulse series.

A proper experiment can be ensured when each bolus is clearly defined. To examine the dependency of the time series signal from the distance between successive labeling pulses, an 8-step label cycling experiment was repeated with different increments of 100 ms, 200 ms, 300 ms and 400 ms starting at TI=800 ms. Thus, the time series ranged from TI=800 ms to 1500 ms, 800-2300 ms, 800-3100 ms and 800-3900 ms, respectively. TR was adjusted to 4500 ms to allow the proper measurement of the longest TI.

All label cycling experiments were performed with and without cardiac triggering. After the trigger signal was received, the slice selective saturation was applied for the imaging slab to erase possible differences in magnetization due to relaxation effects. This was followed by the tagging pulse train.

Conventional ASL time series acquisition was performed without cardiac triggering for inflow times TI=200-3200 ms, equally spaced with increment 200 ms. Total measurement time was 32 min.

Region of interest (ROI) were hand drawn in both conventional and 16-step label cycling data set in corresponding locations. SNR was estimated by dividing grey matter ROI by air ROI.

The label cycling scheme for pulsed ASL disclosed in this patent specification can also be extended to continuous ASL. As presented here, the label and control phase of a continuous ASL experiment should be combined in an appropriate way to allow distinguishing between different inflow times. Again, Hadamard encoding can be used to provide the differentiation, thus enabling continuous ASL to efficiently acquire time series. Testing should be performed to evaluate the behavior of such a technique for different flow scenarios.

The thickness of the slab being labeled and images should be selected such that it is not so thick that labeling would interfere with readout to an extent making it difficult to associate boli with readout signals. A way to avoid such potentially undesirable effects is to use continuous cycled ASL that is generally according to the principle illustrated in FIG. 3 but differs in implementation in that the different combinations of control and labeling pulses are applied in a sequence followed by a sequence of readouts. This differs from the PCASL illustrated in FIG. 1c at least because combinations of control and labeling pulses are used before the readout while in FIG. 1c a readout follows a series of labeling pulseis and another readout follows a series of control pulses.

REFERENCES

1. Kim S G. Quantification of relative cerebral blood flow change by flow-sensitive alternating inversion recovery (FAIR) technique: application to functional mapping. Magn Reson Med 1995; 34(3):293-301.
2. Detre J A, Leigh J S, Williams D S, Koretsky A P. Perfusion imaging. Magn Reson Med 1992; 23(1):37-45.
3. Detre J A, Zhang W, Roberts D A, Silva A C, Williams D S, Grandis D J, Koretsky A P, Leigh J S. Tissue specific perfusion imaging using arterial spin labeling. NMR Biomed 1994; 7(1-2):75-82.
4. Edelman R R, Siewert B, Adamis M, Gaa J, Laub G, Wielopolski P. Signal targeting with alternating radiofrequency (STAR) sequences: application to MR angiography. Magn Reson Med 1994; 31(2):233-238.
5. Alsop D C, Detre J A. Reduced transit-time sensitivity in noninvasive magnetic resonance imaging of human cerebral blood flow. J Cereb Blood Flow Metab 1996; 16(6):1236-1249.
6. Wong E C, Buxton R B, Frank L R. Quantitative imaging of perfusion using a single subtraction (QUIPSS and QUIPSS II). Magn Reson Med 1998; 39(5):702-708.
7. Luh W M, Wong E C, Bandettini P A, Hyde J S. QUIPSS II with thin-slice TI1 periodic saturation: a method for improving accuracy of quantitative perfusion imaging using pulsed arterial spin labeling. Magn Reson Med 1999; 41(6):1246-1254.
8. Parkes L M, Tofts P S. Improved accuracy of human cerebral blood perfusion measurements using arterial spin labeling: accounting for capillary water permeability. Magn Reson Med 2002; 48(1):27-41.
9. Günther M, Oshio K, Feinberg D A. Efficient 3D Perfusion Measurement using Single-Shot 3D-GRASE. Magn Reson Med 2005 (in press).
10. Gunther M, Bock M, Schad L R. Arterial spin labeling in combination with a look-locker sampling strategy: inflow turbo-sampling EPI-FAIR (ITS-FAIR). Magn Reson Med 2001; 46(5):974-984.
11. Hendrikse J, Lu H, van der Grond J, Van Ziji P C, Golay X. Measurements of cerebral perfusion and arterial hemodynamics during visual stimulation using TURBO-TILT. Magn Reson Med 2003; 50(2):429-433.
12. Chao H, Burstein D. Multibolus stimulated echo imaging of coronary artery flow. J Magn Reson Imaging 1997; 7(3):603-605.
13. Golay X, Stuber M, Pruessmann K P, Meier D, Boesiger P. Transfer insensitive labeling technique (TILT): application to multislice functional perfusion imaging. J Magn Reson Imaging 1999; 9(3):454-461.

14. Golay X, Petersen E T, Hui F. Pulsed star labeling of arterial regions (PULSAR): A robust regional perfusion technique for high field imaging. Magn Reson Med 2004; 53(1):15-21.

The invention claimed is:

1. A magnetic resonance imaging (MRI) method comprising:
    labeling blood boli in vivo in an MRI arterial spin labeling process that comprises using different combinations of control and labeling pulses for different time steps and wherein a respective combination of both control and labeling pulses is used in each of a number of said time steps;
    carrying out MRI image readout for each of the time teps to thereby obtain respective readout MRI signals for the respective combinations of control and labeling pulses;
    reconstructing respective intermediate MRI images for the time steps by computer-processing the readout MRI signals; and
    obtaining respective final MRI images identified with selected boli by selectively combining with each other respective sets of the MRI images.

2. A method as in claim 1 in which the time steps follow each other in time.

3. A method as in claim 1 in which the time steps overlap in time such that the labeling of several time steps precedes the step of carrying out the MRI image readouts for those steps.

4. A method as in claim 1 in which the step of obtaining the final MRI images comprises combining the intermediate MRI images according to the elements of selected rows of a selected Hadamard matrix.

5. A method as in claim 1 in which the labeling process comprises labeling the boli in one of said time steps using labeling but not control pulses.

6. A method as in claim 5 in which a tagging cycle of N time steps comprises a time step using only a sequence of labeling pulses and (N−1) time steps each using a respective different sequence of both control and labeling pulses.

7. A method as in claim 1 in which the labeling comprises alternating control pulses and labeling pulses in different sequences for different time steps.

8. A method as in claim 1 comprising using +90°/−90° RF pulses for control pulses and +90°/+90° RF pulses for labeling pulses.

9. An MRI method carried out in a computer-programmed MRI system and comprising:
    encoding each of a number of boli of blood in a patient using control and labeling phases in a respective tagging step of a tagging cycle, wherein each of at least several of the tagging steps comprises encoding with a respective combination that comprises a sequence of both control and labeling phases; and
    extracting respective MRI information for each bolus by obtaining MRI signal for each tagging cycle and selectively combining the MRI signals for respective ones of the tagging cycles.

10. A method as in claim 1 in which the MRI signals (I) for the respective tagging steps relate to the longitudinal magnetization (M) of blood spins associated with the respective times of the tagging steps according to the expression I=EM, where E is an encoding matrix in which each element is a (+1) or a (−1) for control or labeling phase and each row of elements corresponds to a tagging step and the sum along each row is zero except for one row.

11. A method as in claim 10 in which the extracting step comprises carrying out an effective inversion of said expression.

12. A method as in claim 9 in which the each of the tagging steps is followed in time by obtaining the MRI signal for that step.

13. A method as in claim 1 in which a sequence of the tagging steps are carried out before obtaining the MRI signal for the tagging steps in the sequence.

14. A method as in claim 1 comprising using one or two 180° adiabatic inversion pulses for labeling.

15. An MRI system configured through computer programming to provide the following faculties implemented through operation of the MRI system under computer program control, comprising:
    an encoding facility comprising a processor and configured through computer programming of an MRI system to encode each of a number of boli of blood in a patient using control and labeling phases in a respective tagging step of a tagging cycle, wherein each of at least several of the tagging steps comprises encoding with a respective combination that comprises a sequence of both control and labeling phases; and
    an extracting facility comprising a processor and configured through computer programming of an MRI system to extract respective MRI information for each bolus by obtaining MRI signals for each tagging cycle and selectively combining the MRI signals for respective ones of the tagging cycles.

* * * * *